United States Patent [19]

Brown et al.

[11] Patent Number: 5,128,139
[45] Date of Patent: Jul. 7, 1992

[54] COMPOSITION CONTAINING LIPOSOME-ENTRAPPED GRAPEFRUIT SEED EXTRACT AND METHOD FOR MAKING

[75] Inventors: Dell G. Brown; Marc K. Ward, both of Provo, Utah; H. Craig Dees, Knoxville, Tenn.

[73] Assignee: Nu Skin International, Inc., Provo, Utah

[21] Appl. No.: 656,991

[22] Filed: Feb. 15, 1991

[51] Int. Cl.⁵ .......................................... A61K 9/127
[52] U.S. Cl. ................................ 424/450; 424/195.1
[58] Field of Search ....................... 424/195.1, 450; 428/402.2; 264/4.1, 4.3, 4.6; 514/772

[56] References Cited

U.S. PATENT DOCUMENTS

| | | | |
|---|---|---|---|
| 3,890,212 | 6/1975 | Harich et al. | 424/195.1 |
| 4,021,548 | 5/1977 | Harich et al. | 424/195.1 |
| 4,021,577 | 5/1977 | Harich et al. | 424/195.1 |
| 4,021,578 | 5/1977 | Harich et al. | 514/772 |
| 4,485,054 | 11/1984 | Mezei et al. | 424/450 X |
| 4,941,995 | 7/1990 | Richards | 252/407 |

*Primary Examiner*—Thurman K. Page
*Attorney, Agent, or Firm*—Trask, Britt & Rossa

[57] ABSTRACT

A composition is disclosed which comprises a phospholipid mixture and one or more bioactive agents formed into multilamellar liposomes wherein the bioactive agents are bound. Bioactive agents which are particularly suitable to the invention include grapefruit seed extract and Triclosan. A composition for a topical preparation including the multilamellar composition is also disclosed. Methods for preparing the compositions are further disclosed.

25 Claims, No Drawings

COMPOSITION CONTAINING LIPOSOME-ENTRAPPED GRAPEFRUIT SEED EXTRACT AND METHOD FOR MAKING

BACKGROUND

1. Field

This invention relates generally to compositions which include liposome vesicles which entrap substances therein. More specifically, this invention relates to compositions for topical application which comprise liposome-entrapped substances providing bacteriostatic and antibacterial action.

2. State of the Art

In recent years there has been an increase in development of liposomes for use as "containers" for substances which are liberated under specific conditions. Liposomes are small, closed vesicles formed from lipids, particularly phospholipids. Lipids generally have a hydrophobic end or "tail" and a hydrophilic end or "head." When mixed with water, the hydrophobic ends join together toward a common center while the hydrophilic ends become oriented outwardly to interface with the water. More than one layer of lipids, known as a bilayer, forms a liposome having an inner space and an outer surface. Liposomes may have more than one bilayer.

Compositions which include substances encapsulated within the inner space of the liposome have been used in different applications. For example, in U.S. Pat. No. 4,957,735 to Huang dated Sep. 18, 1990, liposomes are used to entrap antibodies for site-specific delivery to disease affected cells within a body. U.S. Pat. No. 4,766,046 to Abra, et al., dated Aug. 23, 1988 discloses the use of liposomes to bind antifungal agents for injection into a body. Bound liposomes are also used in immunoassay procedures as disclosed in U.S. Pat. No. 4,783,400 to Canova-Davis, et al., dated Nov. 8, 1988, and in U.S. Pat. No. 4,874,710 to Piran dated Oct. 17, 1989.

Liposomes have been modified in various ways to provide particular desired properties, such as time-release and site-specific release. Examples of such modifications are disclosed in U.S. Pat. No. 4,921,757 to Wheatley, et al., dated May. 1, 1990 (disclosing methods of making liposomes to respond to a specific stimuli, such as pH or temperature); U.S. Pat. No. 4,766,046 to Abra et al., cited previously, (disclosing formation of liposomes having a particular size); and U.S. Pat. No. 4,708,861 to Popescu, et al., dated Nov. 24, 1987 (disclosing the sequestration of liposomes containing bioactive ingredients in a gel matrix to control release of the bioactive ingredient following injection into a body). The preparation of liposomes is generally discussed in U.S. Pat. No. 4,830,858 to Payne, et al., dated May 16, 1989, the contents of which, specifically at col. 1, line 17 through col. 8, line 4, are incorporated herein by reference. Payne is specifically directed to a spray-dry method for preparing stable liposome precursors.

To date, liposome technology has been directed mainly to use as a carrier for substances, such as drugs, to be injected into a living body. Liposome technology has also been directed to use as a carrier in assay or immunoassay procedures. A detailed discussion of liposomes as carriers is set forth by Ryman, B. E. in "The Use of Liposomes as Carriers of Drugs and Other Cell-Modifying Molecules," Proc. 6th of the Int'l Congr. Pharmacol. 5, 91, published in "Drug Applications," *Clinical Pharmacology*, vol. 5, pp. 91–103, Pergamon Press (1975).

SUMMARY OF THE INVENTION

According to the present invention, a composition for direct topical application is provided which includes liposomes in association with bioactive ingredients. In particular, the bioactive ingredients include grapefruit seed extract which imparts, among other things, bacteriostatic properties to the composition. When bound in liposomes with other bioactive agents, grapefruit seed extract enhances the overall bioactivity of the composition. While liposomes containing grapefruit seed extract may be used in different applications to provide bacteriostatic effects, this disclosure focuses on the use of liposomes containing grapefruit seed extract in the form of a deodorant by way of example.

The present invention provides periodic release, over time, of bioactive agents entrapped within a liposome complex. Periodic release is accomplished, in part, by the use of multilamellar (multilayered) liposomes, formed in multiple layers of liposomes or in clusters. Because liposomes are inherently unstable, they tend to break apart releasing the contents within. When liposomes are layered together, or are in clusters, those liposomes which are confined within or are sandwiched between outer layers of liposomes are more likely to remain stable. Thus, the outer liposomes tend to break apart releasing their contents while protecting the inner liposomes for later degradation and release.

Periodic release of bioactive agents may also be accomplished by modification of the outer liposome surface by addition of certain substances, or by inducing variable shapes and sizes of the liposomes. Thus, those liposomes which have less stable outer surfaces break apart more easily than those which have more complex surfaces due to surface structure or overall shape or size. Periodic release may also be determined and controlled by the entrapment of fragrances in the liposomes, either in addition to the bioactive agents or alone. That is, liposomes which entrap certain fragrances may display increased adherence to the epidermal layers of the skin. As a result, the liposomes, and thus the bioactive agent or agents, tend to remain in contact with the upper skin layers until finally released. In the context of a deodorant, for example, bacteriostatic and antibacterial ingredients bound within liposomes tend to remain in contact with the skin for a longer period of time to provide increased antibacterial protection.

The present invention also provides a means of controlling bacteria, which means is derived from sources in nature. With heightened interest in using predominantly naturally-derived products, a bacteriostatic composition is provided which is essentially derived from natural sources. In prior applications, some components of the means for controlling bacteria have been derived from synthetic, unnatural, or less desirable sources such as fuel oils. Although the lipids used in the present invention for producing the liposome component may be derived from any number of sources, a particularly suitable source is lecithin. A lipid substance derived from lecithin which is high in phosphatidylethanolamines and sphingomyelin is particularly suitable for use in the invention. Phosphatidyethanolamine and sphingomyelin improve the stability of the liposome vesicles and are especially advantageous in promoting healthy cell maintenance and growth.

The bioactive agent-bound liposome composition disclosed herein may be used in many topical applications including deodorants, deodorant soaps, cosmetic preparations, and surgical cleansing preparations. While liposomes, especially those prepared from lecithin extracts, are preferable, other carriers for naturally occurring bacteriostatic and bacteriocidal agents may be used. Micelles encapsulating such agents may be prepared from various non-polar materials in accordance with standard practices known to those skilled in the art of emulsion chemistry. Such micelles may be formed from naturally occurring oils, fats, or the like.

DETAILED DESCRIPTION OF THE PREFERRED EMBODIMENTS

The present invention generally comprises a liposome component, a bioactive substance or substances entrapped in the liposome component, and a base for applying the bioactive substance-bound liposome to the area of application. The bioactive substance or substances include extracts from the seeds of citrus fruits, which extracts display bacteriostatic properties. Citrus seed extracts, such as grapefruit seed extract, are commercially available. Citrus seed extracts generally include vitamin C and proteins. Another bioactive substance which may be used is Triclosan (2,4,4'-Trichloro-2'-hydroxydiphenyl ether) which is an antibacterial agent available from Ciba-Geigy (Greensboro, N.C.) and other suppliers. Triclosan is well known in the art.

In the process of liposome formation, most of the Triclosan and grapefruit seed extract is entrapped within the liposomes. Some Triclosan and grapefruit seed extract may not be entrapped within the liposomes, and it is not necessary to remove or filter out the non-bound material. The presence of non-encapsulated Triclosan and grapefruit seed extract may, when used in a skin-care composition, provide advantageous initial bacteriostatic properties. The liposomes formed by this process may form into multiple layers. The procedure also forms liposomes of various size and shape.

A fragrance may be added to the liposome composition. The amount of fragrance included in the composition may vary, but a preferred amount of fragrance is about 0.5% to about 3% of the total weight of the composition. Quantities of fragrance outside of this preferred range may also be used. That is, smaller amounts of the fragrance may be used, as well as larger amounts. However, larger amounts may adversely affect the structure and stability of the liposomes. When fragrance is added to the formation of liposomes (by addition of water) the liposomes entrap the fragrance, and the fragrance is subject to periodic release. And, as a result, the fragrance will last longer.

Encapsulation of substances, including active ingredients and fragrance, may enhance the associative properties of the liposomes to the outer layers or epidermis of the skin. When liposomes contact the epidermis, degradation of the liposome is reduced and thus release of the encapsulated substance is prolonged. In preferred embodiments, the use of grapefruit oil as a fragrance appears to promote and otherwise enhance the associative properties of the liposome composition.

The Pre-liposome Phospholipid

A pre-liposome phospholipid mixture is used to form the composition of the present invention. The phospholipid mixture generally contains lipids which may be derived from any natural or synthetic source. A particularly suitable lipid for use in the present invention is one derived from natural lecithin and which has a high content of natural phosphatidylethanolamines and sphingomyelin. The phosphatidylethanolamine (PE) content of the mixture may vary, but a preferred percentage is from about five percent to about twenty-five percent of the mixture by weight. Both PE and sphingomyelin are commonly found in lecithin. Both PE and sphingomyelin are known to enhance the growth of eucaryotic cells and, therefore, are advantageous to maintenance of healthy cells and tissue. PE and sphingomyelin enhance the hydrophobic nature of the formed liposomes and enhance the stability of the liposomes. Liposomes which contain PE and sphingomyelin in the surface structure resemble lipid membranes found in nature.

The pre-liposome phospholipid is a mixture which may contain a number of other natural substances such as carotinoids and vitamins.

Preparation of the Liposomes

Example A

A liposome composition was prepared by adding one (I) milliliter (ml) of ethanol to 0.25 grams of pre-liposome phospholipid mixture. The addition of ethanol to the preliposome phospholipid mixture is a solvating step which helps to loosen the phospholipids in the mixture.

The mixture was then co-solubilized with 0.8 grams of grapefruit seed extract P-50 which is available from Chemie Research (Casselberry, Fla.). To the mixture was added 0.5 grams of Triclosan and the mixture was stirred. Finally, four milliliters of distilled water was added to the mixture and mixed rapidly. The addition of distilled water caused the lipid fraction of the mixture to form liposome vesicles.

The foregoing mixture of substances was mixed together at room temperature and was carried out in conventional equipment known to those skilled in the art. No particular equipment or special conditions are required for carrying out the process; it is only necessary that each substance be completely mixed with the preceding ingredient before adding the next ingredient.

Example B

A liposome composition was prepared by co-solubilizing 0.8 grams of grapefruit seed extract with 0.25 grams of pre-liposome phospholipid mixture. To that mixture was added 0.5 grams of Triclosan and the mixture was stirred. Four (4) milliliters of distilled water were then added to the mixture to form the liposomes.

Example C

A liposome composition was prepared by adding one (1) milliliter of ethanol to 0.25 grams of pre-liposome phospholipid mixture with stirring. Then 0.5 grams of Triclosan were added and the mixture was stirred. Thereafter, four milliliters of distilled water were added to the other ingredients to form the liposomes.

Example D

A liposome composition was prepared by adding one (1) milliliter of ethanol to 0.25 grams of pre-liposome phospholipid mixture with stirring. Then 0.8 grams of grapefruit seed extract P-50 were added and the mixture was stirred. Thereafter, four milliliters of distilled water were added to the other ingredients to form the liposomes.

Example E

A liposome composition was prepared by adding 1 ml of ethanol to 0.25 grams of pre-liposome phospholipid mixture. The resulting mixture was co-solubilized with 0.8 grams of grapefruit seed extract. Then 0.09 ml of grapefruit oil, as a fragrance, was added simultaneously with 0.5 grams of Triclosan to the previous mixture and the mixture was stirred. Finally, 4 ml of distilled water were added to the mixture to form the liposome.

Formation of Deodorant Composition

The liposomes produced by the foregoing process may be added to any desirable base to form a variety of compositions, such as deodorant or soap. A particularly suitable composition for use with the formed liposomes is a deodorant base consisting principally of propylene glycol and sodium stearate. Representative of such bases are those referenced in de Nevarre, *The Chemistry and Manufacture of Cosmetics*, Second Edition (Continental Press, Orlando, Fla. 1975) Vol. 3, pp. 224–25 and *Cosmetics and Toiletries* Vol. 100 No. 12 (Allure Publications, Wheaton, Ill.) Dec. 85, pp. 65–67.

A further typical deodorant base formulation is that represented by the following:

| Deodorant Base Formula | Concentrations in % Ranges |
| --- | --- |
| Propylene glycol | 50–75% |
| Aloe vera | <2% |
| Dimethicone copolyol | 5–15% |
| Witch hazel | 5–10% |
| Sodium stearate | 5–10% |
| Cocamide DEA | <5% |
| Water | <2% |

It has been found advantageous to add the liposome composition to the above base when the base is at a temperature of between about 120° F. and about 110° F.

Reference herein to specific details of the processes and compositions disclosed is by way of example and not by way of limitation. It will be apparent to those skilled in the art that many additions, deletions and modifications may be made to the compositions and processes for making the compositions without departing from the spirit and scope of the invention as defined by the following claims.

What is claimed:

1. A composition for periodic release, over time, of entrapped substances comprising:
   a mixture containing phospholipids in the form of multilamellar liposomes, said phospholipids being derived from a natural lecithin source and further including phosphatidylethanolamines and sphingomyelin; and
   citrus fruit seed extract bound within said liposomes.

2. A composition for topical application to the skin of an animal consisting essentially of:
   a mixture containing phospholipids, said phospholipids being in the form of multilamellar liposomes; and
   citrus fruit seed extract bound within said liposomes.

3. The composition according to claim 1 wherein said citrus fruit seed extract is grapefruit seed extract.

4. The composition according to claim 3 further comprising a supplemental bioactive agent bound within said liposome.

5. The composition according to claim 1 wherein said phosphatidylethanolamines comprise from about five percent to about twenty-five percent of said mixture of phospholipids.

6. A composition for periodic release, over time, of entrapped substances comprising:
   a mixture containing phospholipids, said phospholipids being in the form of multilamellar liposomes; and
   an antibacterial bioactive agent bound within said liposomes said agent being 2,4,4'-Trichloro-2'-hydroxydiphenyl ether.

7. A composition for topical application to the skin of an animal consisting essentially of:
   a mixture containing phospholipids, said phospholipids being in the form of multilamellar liposomes;
   citrus fruit seed extract bound within said liposomes; and
   2,4,4'-Trichloro-2'-hydroxydiphenyl ether as a supplemental bioactive agent bound within said liposomes.

8. A composition for topical application to the skin of an animal comprising:
   a mixture containing phospholipids, said phospholipids being in the form of multilamellar liposomes;
   grapefruit seed extract, having bioactive properties, bound within said liposomes; and
   a mixture of propylene glycol and sodium stearate.

9. The composition according to claim 8 further comprising a supplemental bioactive agent bound within said liposomes.

10. The composition according to claim 9 wherein said supplemental bioactive agent in 2,4,4'-Trichloro-2'-hydroxydiphenyl ether.

11. The composition according to claim 8 further comprising fragrance.

12. The composition according to claim 9 further comprising fragrance.

13. A method for preparing a composition for periodic release of entrapped substances comprising:
   providing a mixture containing phospholipids;
   adding an amount of grapefruit seed extract having bioactive properties and mixing together;
   adding an amount of a supplemental bioactive agent to said mixture; and
   adding distilled water and mixing rapidly to form liposomes having said grapefruit seed extract and said supplemental bioactive agent bound therein.

14. The method according to claim 13 further comprising adding an amount of ethanol to said mixture containing phospholipids and mixing with said phospholipids prior to adding said grapefruit seed extract.

15. The method according to claim 14 further comprising adding said formed liposomes to a mixture of propylene glycol, sodium stearate, and water at 110° F.

16. The method according to claim 13 wherein said supplemental bioactive agent is 2,4,4'-Trichloro-2'-hydroxydiphenyl ether.

17. The method according to claim 13 further comprising adding an amount of fragrance to said mixture simultaneously with said addition of said supplemental bioactive agent such that said fragrance becomes bound within said liposomes.

18. The method according to claim 15 further comprising adding a fragrance to said mixture of formed liposomes, propylene glycol, sodium stearate and water.

19. A time-release bacteriostatic skin-care composition comprising:
an emollient base; and
grapefruit seed extract encapsulated in a degradable carrier which degrades over a period of time after contact with animal skin.

20. The skin-care composition of claim 19 wherein said degradable carrier is a liposome.

21. The skin-care composition of claim 20 wherein said liposome additionally contains an antibacterial bioactive agent.

22. The skin-care composition of claim 21 wherein said antibacterial bioactive agent is 2,4,4'-Trichloro-2'-hydroxydiphenyl ether.

23. The skin-care composition of claim 20 wherein said liposome is a multilamellar liposome of phospholipids derived from lecithin.

24. The composition according to claim 4 wherein said supplemental bioactive agent is 2,4,4'-Trichloro-2'-hydroxydiphenyl ether.

25. A composition for topical application to the skin of an animal consisting essentially of:
a mixture containing phospholipids, said phospholipids being in the form of multilamellar liposomes;
citrus fruit seed extract bound within said liposomes;
2,4,4'-Trichloro-2'-hydroxydiphenyl ether as a supplemental bioactive agent bound within said liposomes; and
a fragrance, a substantial amount of which is bound within said liposomes.

* * * * *